US006299905B1

(12) United States Patent
Peterson et al.

(10) Patent No.: US 6,299,905 B1
(45) Date of Patent: Oct. 9, 2001

(54) BIOERODABLE POLYMERIC ADHESIVES FOR TISSUE REPAIR

(75) Inventors: Dale R. Peterson; Z. David Deng, both of Carmel; Todd P. Glancy, Fairmount, all of IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 08/633,102

(22) Filed: Apr. 16, 1996

(51) Int. Cl.$^7$ .......................... A61K 9/10; A61K 32/765; A61K 47/34; C08G 63/08

(52) U.S. Cl. ...................... 424/486; 424/426; 424/78.37; 528/318.4; 528/931; 156/332

(58) Field of Search ..................................... 424/486, 484, 424/426, 428, 448, 78.37; 514/772.7; 528/931, 317.1, 318.4; 156/332

(56) References Cited

U.S. PATENT DOCUMENTS

| | | |
|---|---|---|
| 4,157,418 | 6/1979 | Heilmann . |
| 4,172,934 | 10/1979 | Heilmann . |
| 4,243,775 | 1/1981 | Rosensaft et al. . |
| 4,347,234 | 8/1982 | Wahlig et al. . |
| 4,424,208 | 1/1984 | Wallace et al. . |
| 4,438,198 | 3/1984 | Schmer . |
| 4,440,750 | 4/1984 | Glowacki et al. . |
| 4,595,713 | 6/1986 | St. John . |
| 4,637,905 * | 1/1987 | Gardner . |
| 4,645,503 | 2/1987 | Lin et al. . |
| 4,694,103 | 9/1987 | Krepski et al. . |
| 4,757,128 | 7/1988 | Domb et al. . |
| 4,804,691 * | 2/1989 | English et al. . |
| 4,843,112 | 6/1989 | Gerhart et al. . |
| 4,888,176 | 12/1989 | Langer et al. . |
| 4,902,508 | 2/1990 | Badylak et al. . |
| 4,906,474 | 3/1990 | Langer et al. . |
| 4,956,178 | 9/1990 | Badylak et al. . |
| 5,019,379 | 5/1991 | Domb et al. . |
| 5,075,115 * | 12/1991 | Brine . |
| 5,085,861 | 2/1992 | Gerhart et al. . |
| 5,133,755 | 7/1992 | Brekke . |
| 5,171,579 | 12/1992 | Ron et al. . |
| 5,206,341 | 4/1993 | Ibay et al. . |
| 5,286,763 | 2/1994 | Gerhart et al. . |
| 5,366,508 | 11/1994 | Brekke . |
| 5,464,929 | 11/1995 | Bezwada et al. . |
| 5,475,063 * | 12/1995 | Kaplan et al. . |
| 5,679,723 * | 10/1997 | Cooper et al. . |
| 5,681,873 | 10/1997 | Norton et al. .................... 523/115 |
| 5,824,333 * | 10/1998 | Scopelianos et al. . |

FOREIGN PATENT DOCUMENTS

| | | |
|---|---|---|
| 92111732.1 | 1/1993 | (EP) . |
| 3-45265 | 2/1991 | (JP) . |

OTHER PUBLICATIONS

Anderson, James M. et al., Poly–α–Amino Acids as Biomedical Polymers, Biocompatibility of Tissue Analogs, vol. 1, Chapter 4, pp. 67–88 (1985).

Ferguson, David et al., Bovine Bone Morphogenetic Protein (bBMP) Fraction–induced Repair of Craniotomy Defects in the Rhesus Monkey (*Macaca speciosa*), Clinical Orthopaedics and Related Research, No. 219, pp. 251–258, Jun. 1987.

Ford, James et al., Pharmaceutical Thermal Analysis, Ellis Howard Books in Biological Science, Chapter 2, John Wiley &Sons, New York (1989).

Gerhart, T.N. et al., Antibiotic Release From an Experimental Biodegradable Bone Cement, Journal of Orthopaedic Research, 6:585–592, 1988.

Hollinger, Jeffrey O. et al., Biodegradable Bone Repair Materials, Clinical Orthopaedics and Related Research, No. 207, pp. 290–305, (Jun., 1986).

Hollinger, Jeffrey, Factors for Osseous Repair and Delivery: Part II, J. Craniofac. Surg., 4(3), pp. 135–141, (Jul. 1993).

Hollinger, Jeffrey O. et al., Osseous Wound Healing with Xenogeneic Bone Implants with a Biodegradable Carrier, Surgery, vol. 107, No. 1, pp. 50–54, Jan. 1990.

Hotz, G. et al., Bone Substitute With Osteoinductive Biomaterials–Current and Future Clinical Applications, Int. J. of Oral Maxillofacial Surgery, 23:413–417, 1994.

Kalb, Claudia et al., Hope for Damaged Joints, Newsweek, p. 55, Jan. 29, 1996.

Kamegai, Akihide et al., Bone Formation Under the Influence of Bone Morphogenetic Protein/Self–Setting Apatite Cement Composite as a Delivery System, Bio–Medical Materials and Engineering, vol. 4, No. 4, pp. 291–307, 1994.

Kenley, Richard A. et al., Biotechnology and Bone Graft Substitutes, Pharmaceutical Research, vol. 10, No. 10, pp. 1393–1401, 1993.

(List continued on next page.)

*Primary Examiner*—Edward J. Webman
(74) *Attorney, Agent, or Firm*—Barnes & Thornburg

(57) ABSTRACT

Improved matrices for tissue repair comprising a biocompatible, bioerodable polymer which has a water solubility of about 0.01 to about 500 mg/mL at about 25° C. and adhesive strength of about 600 to about 150,000 Pa; and pressure sensitive adhesives for tissue repair which have adhesive strength of about 600 to about 150,000 Pa. The matrix or adhesive can further comprise a filler or a bioactive agent, or both. The matrices and adhesives are tissue-adherent and dough-like so they can be molded to fit a repair site. When used for bone/implant fixation, or as a filler for bone or cartilage repair, gradual short-term bioerosion of the adhesive matrix allows it to be replaced with developing bone or cartilage tissue. When used for release of a bioactive agent, the agent can be mixed into the adhesive matrix well before the implantation procedure. After implantation, the bioactive agent is gradually released as the adhesive matrix biodegrades.

7 Claims, No Drawings

OTHER PUBLICATIONS

Kohn, Joachim et al., Polymerization Reactions Involving the Side Chains of α–L–Amino Acids, J. Am. Chem. Soc., 109 pp. 817–820, 1987.

Kulkarni, R.K. et al., Polylactic Acid for Surgical Implants, Arch Surg. vol. 93, pp. 839–843, Nov. 1966.

Kulkarni, R.K. et al., Biodegradable Poly(lactic acid) Polymers, J. Biomed. Mater. Res., vol. 5 pp. 169–181, 1971.

Lane, Joseph M. et al., Current Approaches to Experimental Bone Grafting, Orthop. Clin. North Am. 18(2), pp. 213–225, Apr. 1987.

Laurencin, C.T. et al., Bioerodible Polyanhydrides for Antibiotic Drug Delivery: In Vivo Osteomyelitis Treatment in a Rat Model System, Journal of Orthopaedic Research, vol. 11, No. 2, pp. 256–262, 1993.

Leong, K.W. et al., Bioerodible Polyanhydrides as Drug–Carrier Matrices. I: Characterization, Degradation, and Release Characteristics, J. Biomed. Mater. Res., vol. 19, pp. 941–955, 1985.

Lindholm, T.S. et al., Functional Carriers for Bone Morphogenetic Proteins, Annales Chirurgiae at Gynaecologiae, No. 82, pp. 3–12, 1993.

Lovell, T.P. et al., Augmentation of Spinal Fusion with Bone Morphogenetic Protein in Dogs, Clinical Orthopaedics and Related Research, No. 243, pp. 266–274, Jun., 1989.

Miki, Takashi et al., Effect of Freeze–Dried Poly–L–Lactic Acid Discs Mixed with Bone Morphogenetic Protein on the Healing of Rat Skull Defects, J. Oral. Maxillofac. Surg., No. 52, pp. 387–391, 1994.

Miyamoto, Shimpei et al., Evaluation of Polylactic Acid Homopolymers as Carriers for Bone Morphogenetic Protein, Clinical Orthopaedics and Related Research, No. 278, pp. 274–285, May, 1992.

Miyamoto, Shimpei et al., Polylactic Acid–Polyethylene Glycol Block Copolymer, Clinical Orthopaedics and Related Research, No. 294, pp. 333–343, Sep., 1993.

Miyamoto, S. et al., Bone Induction and Bone Repair by Composites of Bone Morphogenetic Protein and Biodegradable Synthetic Polymers, Annales Chiurugiae et Gynaecologiae, No. 82, pp. 69–76, 1993.

Pinholt, Else Marie et al., Bone Induction by Composites of Bioresorable Carriers and Demineralized Bone in Rats: A Comparative Study of Fibrin–Collagen Paste, Fibrin Sealant, and Polyorthoester With Gentamicin, J. Oral Maxillofac. Surg., 50:1300–1304, 1992.

Pulapura S. et al., Biomaterials Based on "Pseudo"–Poly(Amino Acids): A Study of Tyrosine Derived Polyiminocarbonates, Polymer Preprints, vol. 31, No. 1, pp. 233–234, Apr. 1990.

Rokkanen, Pentti U., Absorable Materials in Orthopaedic Surgery, Ann. Med., No. 23, pp. 109–115, 1991.

Sidman, K.R. et al., Biodegradable, Implantable Sustained Release Systems Based on Glutamic Acid Copolymers, Journal of Membrane Science, vol. 7, No. 3, pp. 277–291, 1980.

*Sigma Chemical Company :Biochemicals Organic Compounds and Diagnostic Reagents*, pp. 1963–1965, (1996).

Storey, Robson F. et al., Novel Synthesis of (Carboxylic Acid)–Telechelic Poly(ε–Caprolactone), Abstracts of Papers of the American Chemical Society, 1996, V.211, Mar. 24, pp. 113–114.

Storey, Robson F. et al., New Epoxy–Terminated Oligoesters: Precursors to Totally Biodegradable Networks, Journal of Polymer Science: Part A: Polymer Chemistry, vol. 31, pp. 1825–1838, 1993.

Stupp, Samuel I. et al., Organoapatites: Materials for Artificial Bone. I. Synthesis and Microstructure, Journal of Biomedical Materials Research, vol. 26, 169–183, 1992.

Stupp, Samuel I. et al., Organoapatites; Materials for Artificial Bone. II. Hardening Reactions and Properties, Journal of Biomedical Materials Research, vol. 27, 289–299, 1993.

Stupp, Samuel I. et al., Organoapatites: Materials for Artificial Bone. III. Biological Testing, Journal of Biomedical Materials Research, vol. 27, pp. 301–311, 1993.

Wei, Guoxiong et al., A Bioabsorable Delivery System for Antibiotic Treatment of Osteomyelitis, J. Bone Joint Surg. [Br], vol. 73–B, No. 2, pp. 246–252, 1991.

Cerrai, et al., "Block copolymers from L–lactide and poly(ethylene glycol) through a non–catalyzed route", *Makromol. Chem., Rapid Commun.*, 14, pp. 529–538 (1993).

Hackh's Chemical Dictionary $5^{th}$ ed., pp. 1–3, 1987.*

* cited by examiner

BIOERODABLE POLYMERIC ADHESIVES FOR TISSUE REPAIR

SUMMARY OF THE INVENTION

In a matrix for tissue repair comprising a biocompatible, bioerodable polymer, this invention provides the improvement wherein the polymer has a water solubility of about 0.01 to about 500 mg/mL at about 25° C. and an adhesive strength of about 600 to about 150,000 Pa so that the matrix is tissue adherent. One such matrix comprises a polymer that also has a glass transition temperature of less than 0° C. The improved matrices are useful for repairing tissues such as bone and cartilage, and for administering biologically active substances.

These improved matrices may further comprise a filler, a bioactive agent, or both.

In another aspect, this invention provides a pressure sensitive adhesive for tissue repair comprising (a) a biocompatible, bioerodable polymer which exhibits adhesive strength of about 600 to about 150,000 Pa, (b) a filler and (c) a bioactive agent. Further, this invention provides a pressure sensitive adhesive for tissue repair comprising a terpolymer of an a-hydroxycarboxylic acid which exhibits adhesive strength of about 600 to about 150,000 Pa.

This invention also relates to methods for repairing bone or cartilage which comprise applying to the bone or cartilage an implant matrix of this invention.

In the methods of repairing bone or cartilage using a bioerodable implant matrix, this invention further provides the improvement comprising using a tissue-adherent implant matrix of this invention to repair the defect.

In another aspect this invention relates to implantable articles of manufacture for use in the release of a bioactive agent into a physiological environment, said articles comprising a biologically active agent disbursed in an implant matrix of this invention.

DETAILED DESCRIPTION OF THE INVENTION

The present invention is directed to improvements in matrices for tissue repair comprising biocompatible, bioerodable polymers. In one improvement, the matrix comprises a polymer which has a water solubility of about 0.01 to about 500 mg/mL at about 25° C. and an adhesive strength of about 600 to about 150,000 Pa so that the matrix is tissue adherent. One such matrix comprises a polymer that has a glass transition temperature of less than 0° C. The improved matrix can further comprise a filler or a bioactive agent, or both. An especially useful attribute of the improved matrices is that the matrix adheres to tissues such as bone or cartilage. In addition, the matrix has a texture like that of dough or putty; thus, it is particularly suitable for being molded to fit into a site needing repair.

In another aspect, this invention provides pressure sensitive adhesives for tissue repair comprising (a) a biocompatible, bioerodable polymer which exhibits adhesive strength of about 600 to about 150,000 Pa, (b) a filler and (c) a bioactive agent. Further, this invention provides pressure sensitive adhesives for tissue repair comprising a terpolymer of an α-hydroxycarboxylic acid which exhibits adhesive strength of about 600 to about 150,000 Pa.

The implant matrices and adhesives of this invention can be applied to the bone-contacting surfaces of prosthetic appliances (as a cement), or they can be inserted into and around bone defects and cavities or cartilage surfaces (as a filler). The matrix or adhesive biodegrades gradually. As it biodegrades, it is replaced by developing bone or cartilage tissue in a manner which permits a natural healing of the tissue. Thus, it provides an effective means for treating or repairing bone or cartilage.

When the matrix or adhesive further comprises a bioactive agent, it serves as a depot device for release of the bioactive agent. Release of the agent occurs as the matrix or adhesive biodegrades after implantation.

Many attempts have been made to develop a repair matrix that could facilitate bone or cartilage repair and also deliver bioactive agents such as growth factors. Such a matrix could be used instead of bone grafts. Thus far, only matrices comprised of natural products such as collagen have shown promise. Collagen, however, is difficult to manufacture and control in order to meet regulatory standards. In addition, surgeons are not satisfied with collagen matrices because they are difficult to form and/or handle.

Other approaches to replace bone grafts have included conventional bioresorbable polymers, ceramics such as tricalcium phosphate (TCP), natural polymers, such as collagen, proteoglycans, starches, hyaluronic acid and modified bone matrix. To date these efforts have only produced delivery matrices which (a) impede healing, (b) provoke negative tissue reactions, (c) cannot be sterilized, (d) are difficult to use or (e) cannot be manufactured to the satisfaction of regulatory bodies.

For example, one approach was to use conventional bioresorbable polymers such as polylactide-co-glycolide (PLG) to administer growth factors. It was very difficult, however, to combine PLG with the growth factor without inactivating the growth factor. Other disadvantages encountered with PLG were that, when it was implanted, it inhibited the bone healing response and occasionally caused aseptic sinus tract and inflammation and destroyed surrounding bone.

Another attempt to develop an effective bone repair matrix involved implanting a bone growth factor absorbed on a ceramic such as TCP. The problem with this approach was that the TCP particles migrated out of the defect area too quickly to deliver the growth factor effectively.

A major problem encountered with previously tried delivery systems is that the bioerodable material could not be mixed with the growth factor prior to the time of surgery. Mixing the delivery matrix with the bioactive material immediately prior to, or during, the surgery process is very awkward and can lead to inconsistent results.

The bioerodable matrices and adhesives of this invention solve several of the problems encountered with previous delivery systems. They are especially useful in the delivery of bioactive proteins such as growth factors because the polymer component dissolves in solvents which are compatible with proteins. Thus, it is possible to formulate the bioactive component in the polymer adhesive matrix in advance, i.e., well before a surgical procedure, under acceptable regulatory conditions, including sterilization of the product without inactivating the bioactive components. Quality control during the preparation of delivery systems using the present adhesive products is, therefore, greatly improved.

Other advantages of the polymer implant matrices and adhesives of this invention are that they are biocompatible and bioerodable in vivo. The term "biocompatible" means that the polymer is non-toxic, non-mutagenic and, at most, elicits only a minimal to moderate inflammatory reaction. The term "bioerodable" means that the polymer either degrades or is resorbed after implantation into products that are used by, or are otherwise eliminated from, the body by existing biochemical pathways.

The present matrices comprise polymers that are bioerodable within a period of from about three hours to about two years. This period can be varied, depending upon the desired application. A preferred period is from about one day to about one month; another preferred period is from about two weeks to about three months. The period for bioerosion is the time after which the polymer will no longer be detectable at the site of implantation, using standard histological techniques.

Thus, an important advantage of the present polymer implant matrices is that a second surgical procedure to remove the matrix is not required because it degrades with time, and its degradation products are absorbed by the body.

One required feature of certain of the adhesive bioerodable polymers useful in the improved matrices of this invention is their water solubility. They are soluble in water at about 0.01 to about 500 mg/mL of water at about 25° C. (ambient temperature). Typically, the polymers are soluble in water at about 0.1 to about 500 mg/mL of water. Preferably they are soluble at about 5 to about 400 mg/mL of water.

Some investigators have reported aseptic necrosis, inflammation, or sinus tracts in animals where poly($\alpha$-hydroxycarboxylic acid) implants have been used. It is generally thought that these adverse reactions were caused by local acidosis from the degradation of the polymer. Use of more soluble ionomer forms of the polymers avoids the danger of developing local acidosis at implant sites because the polymers dissolve and are diluted or carried away before quantities of acidic degradation products are produced.

This water solubility allows the polymers to be more readily dissolved by serum at the surface of the implant matrix and thereafter distributed into surrounding body fluids where they can be mobilized for hydrolysis at remote sites. This feature is important because hydrolysis of some polymers results in a localized pH gradient which can be adverse to local cell growth. Hydrolysis occurring at the implant site produces an unnatural concentration of hydrolysis products (and increased acidity) at the surface of the matrix. Such acidity can easily interfere with ongoing tissue repair. The water soluble polymers used in the improved matrices of this invention, therefore, preserve conditions that optimize a localized environment for cell viability and growth at the implant surface.

Certain polymers used in the matrices of this invention, the polyesters, have a glass transition temperature (Tg) of less than 0° C. When used with a filler, polymers with a Tg of less than 0° C. have excellent handling properties.

A required feature of all the polymers for use in the matrices and adhesives of this invention is a threshold level of adhesiveness. Adhesiveness has been found to be important for optimizing implant performance. Adhesiveness is an intrinsic property that is not readily correlated with polymer properties, but can easily be assessed empirically. Adhesiveness is a characteristic that derives from a wide variety of polymer parameters, including polymer type, i.e., the nature of the covalent linkages linking the monomers, molecular weight and intrinsic structure and as well the nature of the surface to which the matrix will be adhered. Skilled practitioners in the art can readily assess polymer adhesive properties using known techniques, such as those illustrated in the examples infra.

The polymers used in the matrices and adhesives of this invention exhibit adhesive properties on different substrates, such as, for example, dry substrates like glass and water-swollen poly(2-hydroxyethyl methacrylate) ("pHEMA") on glass, which simulates wet tissues. Typically, the polymers withstand a maximum stress on a glass substrate of about 1,000 to about 150,000 Pa, preferably about 10,000 to about 40,000 Pa, and most preferably, about 12,000 to about 16,000 Pa. The polymers withstand a maximum stress on a pHEMA substrates of about 600 to about 90,000 Pa, preferably about 2,500 to about 40,000 Pa, and most preferably about 5,500 to about 8,500 Pa. Thus, the range of adhesive strength is from about 600 to about 150,000 Pa.

The polymers are moldable by hand at a temperature of about 60° C. or below. Typically, they are moldable at about 4° C. to about 60° C., preferably at about 15° C. to about 50° C., and most preferably at about 20° C. to about 30° C. The degree of moldability at a selected temperature is dependent upon the characteristics of the polymer selected as well its molecular weight. The matrix containing the polymer remains moldable after it has been implanted within the body.

A variety of polymers can be used in the matrices and adhesives of this invention. The polymers must be biocompatible and susceptible to rapid biodegradation in order to be replaced by new tissue. The polymers may be homopolymers, terpolymers, copolymers, blocked copolymers, or blends of polymers. Bioerodable polymers include polyanhydrides, polyorthoesters, polyesters (such aS polylactic acid (PL), polyglycolic acid (PG), polyhydroxybutyric acid, polymalic acid, polyglutamic acid and polylactones) and poly(amino) acids.

One type of polymer especially useful in the matrices and adhesives of this invention is a polyester ionomer, more particularly, a non-toxic salt of a bioerodable carboxy-terminated polyester of the general formula RO~PE~COOH or HOOC~PE~COOH wherein R is hydrogen or $C_1$–$C_4$ alkyl and ~PE~ is a divalent residue of a polyester. The polyester can comprise a homopolymer, copolymer, or terpolymer of biocompatible hydroxy acids, for example, lactic acid, glycolic acid, $\epsilon$-hydroxycaproic acid, and $\gamma$-hydroxyvaleric acid. Alternatively, the polyester can be formed using copolymerization of a polyhydric alcohol and a biocompatible polycarboxylic acid. Most typically such copolymers are formed between dihydric alcohols, for example, propylene glycol for biocompatibility and biocompatible dicarboxylic acids. Representative carboxylic acids for formation of the polyesters useful for preparing these polyester ionomers include a Kreb's cycle intermediate such as citric, isocitric, cis-akonitic, $\alpha$-ketoglutaric, succinic, maleic, oxaloacetic and fumaric acid. Many of such carboxylic acids have additional functionalities which can enable further cross-linking of the polymers if desirable.

The polyesters can be further modified, for example, by reaction with a cyclic carboxylic anhydride to convert residual hydroxy functionality to the carboxy-terminated forms useful for preparation of these polyester ionomers.

The carboxy-terminated polyesters used to prepare the polyester ionomers are selected to have a threshold water solubility between about 0.01 and about 500 mg/mL of water, preferably about 0.5 to about 350 mg/mL of water, at ambient temperature. The polyester precursors have a weight average molecular weight of about 400 to about 10,000, more typically about 1,000 to about 5,000. Conversion of these compounds by neutralization with pharmaceutically acceptable bases produces polyester ionomers having enhanced water solubility relative to the carboxy-terminated polyester precursors but retaining other polymer functionality.

The polyester ionomers are prepared from mono- or bis-carboxy-terminated polyesters. Generally, the carboxy-terminated polyester is dissolved in an organic solvent and neutralized by the addition of a stoichiometric amount of a physiologically acceptable base. In one embodiment, the neutralization is carried out with less than a stoichiometric amount of base to produce a composition comprising a carboxy-terminated polyester and its corresponding ionomer, the ratio of those components being dependent on the degree of neutralization. Suitable bases for use in forming the polyester ionomers include hydroxides of Group Ia or Group IIa metals including preferably the hydroxides of lithium, sodium, potassium, magnesium and calcium, as well as physiologically compatible salt-forming amines. Following neutralization of the carboxy-terminated polyester, the resulting ionomer can be isolated using standard isolation techniques. the ionomer is typically dried prior to use in fabrication of implant matrices and adhesives.

The carboxy-terminated polyesters can be prepared using art-recognized procedures for polyester synthesis. The carboxy-terminus (or termini) on such compounds can be formed by reaction of hydroxy functional polyesters with, for example, a stoichiometric amount of a cyclic anhydride of a $C_1$–$C_6$ dicarboxylic acid, such as succinic anhydride.

Bis-hydroxy functional polyesters are readily prepared by reaction of a dihydric alcohol initiator, for example, propylene glycol or ethylene glycol, with one or more cyclic hydroxy acid esters, for example lactide, glycolide or caprolactone. Reaction of such bis-hydroxy functional polyesters with cyclic anhydrides produces bis-carboxy functional polyesters that can be used to prepare the ionomers described supra.

The polyester prepolymers used for the preparation of the ionomers can be prepared using art-recognized polyester-forming reaction chemistry, typically using, for example, metal catalysts to promote ester-forming reactions. One problem with the prior art procedures is the difficulty in removing the metal catalyst from the product polyesters. Removal of the catalyst is particularly crucial when the polyesters are intended for use in medical applications.

It has been found that polyesters of hydroxy acids can be prepared in high yields and high purity with good control over structure/functionality by reacting the corresponding cyclic esters with a hydroxy functional initiator at elevated temperatures under substantially anhydrous conditions. Thus, one preferred method for preparing the polyesters consists of reacting an initiator, for example, a mono-hydric or dihydric alcohol, with at least one cyclic hydroxy acid ester under substantially anhydrous conditions at elevated temperatures. The reaction is preferably carried out neat (an absence of solvent) at a temperature of about 100–180° C., more preferably about 120–1600° C. The term "substantially anhydrous conditions" means that routine efforts are made to exclude water from the reaction mixture and can typically include such steps as pre-drying the reaction vessel with heat and carrying out the reaction under drying conditions.

The structure of the polyester is controlled by selection and stoichiometry of the cyclic hydroxy acid ester reactant (s) and the amount of initiator used with lower relative initiator amounts leading to higher average molecular weight product and higher relative amounts of initiator leading to lower average molecular weight product.

The hydroxy functional initiator can either be a monohydric alcohol, for example a $C_1$–$C_4$ alkanol, or a di-or polyhydric alcohol. Alternatively, the hydroxy functional initiator can be a hydroxy acid, for example glycolic acid.

The product hydroxy-terminated polyesters can be converted to a carboxy-terminated polyester that can be used to prepare the polyester ionomers by reaction with a stoichiometric amount of a cyclic anhydride.

The method for preparing polyester polymers for use in preparing the polyester ionomers can be carried out as well in the presence of a cyclic carboxylic acid anhydride to provide directly the corresponding carboxy terminated polyester compound. The reaction is carried out under the same conditions described supra for preparing the polyester. Most typically the reaction is carried out using about equimolar amounts of a monohydricalcohol initiator and the cyclic anhydride. Where the initiator is a dihydric alcohol, the molar ratio of the cyclic anhydride to the initiator is preferably raised to about 2:1.

Preferred polyester ionomers are those made up of lactide, glycolide and caprolactone or valerolactone. Polymers of lactide/glycolide/caprolactone (PLGC) are especially beneficial. PLGC terpolymers having a molecular weight in the range of about 1,000 to 3,000 are especially preferred. Terpolymers wherein the lactide and glycolide each make up about 35–45% of the terpolymer, and the caprolactone or valerolactone make up about 10 to about 30% of the terpolymer are particularly useful.

Selected poly(amino acids) are another type of polymer useful in the matrices and adhesives of this invention. Certain poly(amino acids) exhibit adhesive properties toward connective tissue, such as cartilage and bone. The poly(amino acid) can be: (1) a classic poly(amino acid) of the formula $H_2N$—Q—$COOR_2$ in which Q is the divalent residue of a polypeptide and $R_2$ is H, a metal cation, or ammonium, or (2) a pseudo-poly(amino acid).

The matrix may comprise two or more different poly (amino acids), each of the formula $H_2N$—Q—$COOR_2$ wherein:

Q is a divalent residue of a polypeptide formed from 1 to 3 species of amino acids;

the amino acid components of Q are represented by the formula aX +bY +cZ;

wherein a, b, and c represent the respective mole fractions of the amino acids X, Y, and Z; a=0 to 1, b=0 to 1, and c >0 but <1; and a+b+c=1.0;

X is selected from glutamate, asparagine, aspartate, and glutamine;

Y is selected from lysine and arginine; and

Z is selected from cysteine, methionine, serine, threonine, glycine, alanine, valine, leucine or isoleucine.

Alternatively, the matrix may comprise a divalent or multivalent monomer and a poly(amino acid) of the formula $H_2N$—Q—$COO_2$ as defined supra wherein the Q polypeptide is formed from 1 to 3 species of amino acids.

A wide variety of polypeptides in a wide variety of ratios may be used to form the useful poly(amino acids). The polypeptides are available commercially from Sigma Chemical Company, P.O. Box 14508, St. Louis, Mo. 63178.

Certain amino acid homopolymers, however, are not useful in the matrices. For example, amino acids with aliphatic side chains do not interact well enough with biological surfaces. They may, however, be used as chain extenders or modulators, along with cysteine, methionine, serine, and threonine, in mixed polymers. Amino acids with aromatic side chains exhibit low rates of diffusion in the body and are, therefore, not suitable to be components of selected poly(amino acids). Histidine is also not a suitable component due to its limited interaction with biological surfaces. Histidine may, however, be used to complex with the polyamino acids as a monomer.

Particular divalent or multivalent monomers may be used in combination poly(amino acids) in the matrices. Amino acids with two or more positive charges at physiological pH, such as lysine, arginine, or histidine, form complexes with poly(amino acids) bearing negative charges at physiological pH. Likewise, amino acids with two or more negative charges, such as aspartate or glutamate, can form complexes with poly(amino acids) bearing positive charges.

In the pseudo-poly(amino acids) that can be selected, the dipeptide monomers are covalently bound through other than normal peptide linkages. Pseudo-poly(amino acids) suitable for use are those having the requisite adhesive character. They can be prepared using the chemistry described, for example, in Kohn, J. and Langer, R., *Polymerization Reactions Involving the Side Chains of α-L-Amino Acids, J. Amer. Chem. Soc.,* 109, 917 (1987) and Pulapura, S. and Kohn, J., *Biomaterials Based on "Pseudo"-Poly(Amino Acids): A Study of Tyrosine-Derived Polyiminocarbonates, J. Polymer Preprints,* 31, 23 (1990), which are incorporated by reference. The pseudo-poly (amino acids) can be used alone or in combination with a classic poly(amino acid) or with a different pseudo-poly (amino acid).

As discussed supra, the composition of the polymer, as well as the molecular weight and physical properties, can be varied. Those in the art will also appreciate that compounds can be mixed into, or polymerized with, the polymer as required for additional strength or other desirable physical properties, using materials known in the art. For example, TCP or other ceramic-type materials that provide increased viscosity can be added to the composition.

The dissolution rate of polymers such as the PLGC terpolymers can be varied by end group modification. For example, PLGC terpolymers with OH end groups degrade very slowly; PLGC terpolymers wherein the OH end groups have been partially neutralized, e.g., by neutralization of about 40 to 60% of the end groups with sodium hydroxide, degrade at a moderately slow rate; and PLGC terpolymers wherein most the OH end groups have been neutralized, e.g. by sodium hydroxide, degrade within a few days. Exemplary end groups are OH and COONa+, but any ion or functional group that can be placed on the polymers could be used. The amount of end group modification can have a dramatic effect on the dissolution rate.

In addition to end group changes, variations of molecular weight and composition can be selected to prepare suitable compositions. Increases in molecular weight increase the time to dissolution. Also, blending in a high NW polymer will increase the time to dissolution, or blending in a low MW polymer will decrease the time.

In general, when the matrix is used to repair bone defects, the polymer is selected to degrade over a period of three hours to two years. Preferably, the polymer will degrade in about one month, most preferably in about two weeks. The desired degradation time will depend on the nature of the repair site, including the local tissue type, the support function being served by the implanted matrix, and the nature and concentration of the bioactive component, if any, in the implant matrix. Targeted degradation times can be achieved by selection of polymer/filler combinations on an individual basis.

In the matrix, the polymer may be combined with a bioactive agent, one or more fillers, or both. When the matrix contains a filler, it typically contains about 1 to about 90 weight percent filler, preferably about 30 to about 70 weight percent, and most preferably about 35 to about 50 weight percent of filler.

The filler may be particulate, fibrous, organic, inorganic or a mixture of organic and inorganic. Suitable fillers include bone chips, tricalcium phosphate, hydroxylapatite ("HA"), small intestine submucosa ("SIS" as described in U.S. Pat. Nos. 4,902,508, issued Feb. 20, 1990, and 4,956,178, issued Sep. 11, 1990), bioglass granules, synthetic polymers, calcium carbonate, calcium sulfate and collagen, or other extracellular matrix compound, or various mixtures thereof.

When the filler is particulate, the average particle size is from about 20 $\mu$m to about 2,000 $\mu$m, more preferably about 75 to about 700 $\mu$m, and most preferably, about 100 $\mu$m to about 500 $\mu$m.

As discussed supra, the implant matrix may contain a bioactive agent or agents. A bioactive agent is a compound or material that affects the living cells in its surrounding environment, e.g., it acts to enhance the healing process.

Bioactive agents preferred for use in the present invention are growth factors, growth factor binding proteins or cells. Examples of suitable growth factors include: a fibroblast growth factor, a transforming growth factor (e.g., TGF-$\alpha_1$), a bone morphogenetic protein, epidermal growth factor, an insulin-like growth factor or a platelet-derived growth factor.

Examples of growth factor binding proteins are insulin-like growth factor binding proteins (IGFBP's) such as IGFBP's 3 and 5. Examples of suitable cells include bone marrow cells and mesenchymal stem cells. The bioactive material can also be an osteogenic agent which stimulates or accelerates generation of bone upon implantation into a bone defect site. Examples of osteogenic agents include demineralized bone powder, morselized cancellous bone, aspirated bone marrow, bone forming cells, and other bone sources.

The bioactive agent may also be an antibacterial substance. Examples of useful antibacterial agents include gentamicin and vancomycin.

When a bioactive agent is included in the matrix or adhesive, it is incorporated in amounts of from about $10^{-5}$% to about 33% by weight of the matrix. Typically, the agent is incorporated at a rate of from about $10^{-2}$% to about 20% by weight of the matrix. A preferred rate of incorporation is from about $10^{-1}$% to about 5% by weight.

When the bioactive agent is a growth factor, it is generally incorporated into the matrix or adhesive in amounts from about 10% to about 1% by weight of the matrix. When cells are the active component, the range is from about 0/5% to about 50% by weight. When using an agent such as demineralized bone, bone marrow and the like, the range is preferably from about 5% to about 95% by weight. For TGF-$\alpha_1$ the preferred range is from about $10^{-4}$% to about 0.05% of TGF-$\alpha_1$ by weight of the matrix.

The percent of bioactive agent should be such that it will release from the implanted matrix in vivo in an effective manner, generally over a period of from about a day to about 30 days and longer, depending on the nature and application of the composition.

The release rate of a bioactive agent, such as TGF-$\alpha_1$, can be varied by modification of the polymer as discussed supra, e.g., by varying its end groups, molecular weight or composition.

Other agents that may be added to the matrix include: an extract from whole blood, packed red cells, platelets, plasma (fresh or fresh frozen), serum, skin, bone, cartilage, tendon or microorganisms; synthetic proteins, etc. Suitable proteins can be any one of a wide variety of classes of proteins, such as keratins, collagens, albumins, globulins, hormones, enzymes, or the like. The material can be simple peptides, simple proteins, or conjugated proteins, such as glycoproteins, mucoproteins, lipoproteins, heme proteins, nucleoproteins, or the like.

Antioxidants may also be included in the matrix. Antioxidants suitable for use include tocopherol, citric acid, butylated hydroxyanisole, butylated hydroxytoluene, tert-butylhydroquinone, propyl gallate, sodium ascorbate, and other antioxidants which are "generally recognized as safe" by the Food and Drug Administration.

Thus, the implant matrices can be prepared by blending the polymer with one or more bioactive agents and optionally other excipients, for example, additives to optimize retention of biological activity and polymer functionality during sterilization, and then by sterilizing and packaging the implant formulation for surgical use.

Sterilization can be accomplished by radiation with about 1 to about 3 mRad of gamma radiation or electron beam radiation. If the bioactive agent is a protein or peptide, biological activity can be optimized during sterilization by including in the formulation 1) an extraneous protein, for example albumin or gelatin; and 2) a free radical scavenger (antioxidant), for example propyl gallate, 3-tert-butyl-4-hydroxyanisole (BHA) or ascorbic acid, in amounts effective to retard radiation-induced degradation of the biologically active peptide. The sterilization is preferably conducted at low temperature, for example −70° C.

When a filler is used in the matrix with a biologically active peptide or protein, it is advantageous to form a mixture of the biologically active compound and an extraneous protein such as albumin or gelatin, and coat the filler with that formulation prior to blending the filler into the polymer.

Preferred matrices for bone repair include the following:

| Ingredient | Most Preferred Amount (mg) | Range of Preferred Amount (mg) |
| --- | --- | --- |
| TCP (or SIS) | 100 | 10–500 |
| Polymer* | 200 | 20–500 |
| Gelatin | 10 | 1–100 |
| TGF-$\beta_1$ and/or | $10^{-2}$ | $10^{-4}$–$10^{-1}$ |
| Cells | 100 | 10–200 |
| Antioxidant | 2 | 0.5–50 |

*Preferred Polymer: PLGC COONa - 40:40:20 (MW = 2000)

The implant matrices of this invention can be prepared using standard formulation techniques. If the matrix includes a bioactive agent, the polymer can be mixed with the agent or used to encapsulate it, again using known methods such as mixing and compressing and microencapsulation.

This invention also provides an implantable article of manufacture for use in the release of a bioactive agent into a physiological environment comprising a biocompatible tissue-adherent implant matrix of this invention and one or more bioactive agents. Preferred implantable articles are those wherein the bioactive agent is a growth promoting factor.

Although the polymers have been described for use in repairing tissues such as bone and cartilage and in a delivery matrix for a bioactive agent in vivo, these descriptions are illustrative only and are not intended to be limiting in any way. There are many other applications for the bioerodable adhesive polymers of this invention.

For example, the polymers can be used in the treatment of bone tumors. Such treatment typically involves excision of the tumor as well as portions of the surrounding bone, leaving a large cavity in the bone. A graft using autogenous bone (bone harvested from another site in the patient's body) is the conventional and accepted technique for filling such bony defects. Although use of autogenous bone provides rapid incorporation of new bony ingrowth into a bone cavity, this procedure is associated with a morbidity caused by the required surgical exposure needed to harvest the patient's bone. Moreover, some patients, particularly osteoporotic individuals, have very limited amounts of bone that are appropriate for use as a graft.

Alternatively, allografts, i.e., bones taken from other individuals, may be used as bone-grafting material. There are certain risks associated with such allografts, however, including the transfer of infections and even unrecognized malignant cells from the harvested patient to the grafted patient as well as the problem of immunologic barriers between all individuals. Furthermore, these processes are complicated and labor-intensive. Thus, the implant matrices of this invention offer a distinct improvement over traditional treatments for bone tumors.

The polymers used in the matrices and adhesives of this invention are typically prepared so that they form a viscous adhesive rather than a conventional solid. When the polymer is mixed with a particulate filler to form the biocompatible matrix or adhesive, the polymer can be used to coat the particles of filler. An example of a suitable particulate filler is a ceramic such as TCP. When the particles are coated with the polymer adhesive, they form a self-adherent dough-like substance that can be conveniently molded to fit surgically into bone defects. When a bioactive agent, such as a protein growth factor, is to be included in the matrix, it can be absorbed onto the particles of the biocompatible solid filler prior to being coated with the polymer adhesive.

This invention also relates to improvements in methods of repairing bone or cartilage using a bioerodable implant matrix, wherein the improvement comprises using a tissue-adherent matrix of this invention to repair the bone or cartilage.

Preferred improvements are those wherein the matrix contains a bioactive agent, particularly those wherein the bioactive agent is a growth-promoting factor.

When using a matrix of this invention to repair bone or cartilage, a surgeon, physician or other caregiver first determines the size of the cavity or void to be filled, or the dimensions of the repair site, and removes the appropriate amount of polymer adhesive matrix from packaging. Typically, the packaging is a barrier package which prevents water vapor from contacting the polymer in the composition; however, it is understood that the packaging may be any one of a wide variety of containers.

Following removal from the packaging, the surgeon then molds the adhesive implant matrix at ambient temperature into dimensions compatible with the repair site. In the case of bone repair, the matrix is molded to the dimensions of the cavity or void to be filled. In the case of connective tissue repair, it is molded to fit the dimensions of the repair site. The adhesive matrix is then applied to the cavity or repair site in a manner which permits it to adhere to the bone or cartilage for a time sufficient to effect its repair. Typically, the surgeon presses the molded matrix against the damaged, and often wet, tissue. Because the matrix has adhesive properties, when it is applied to the surrounding bone or connective tissue with pressure, it will stick and remain in place long enough to effect repair of the bone or tissue.

When the matrix contains a bioactive agent, it is typically implanted in a site in the body where a concentration of the bioactive agent would be beneficial. Thus, for example, in the treatment of an osteoporosis-induced fracture involving a void or bony defect, an implant matrix containing a growth-promoting agent is molded to conform to the bone defect or cavity and is inserted by the surgeon at that location. Similarly, the matrix can be implanted or injected into soft tissue for sustained drug release.

PREPARATION

Poly(lactide/glycolide/ε-caprolactone) Ionomer

Instrumentation. Gel permeation chromatography (GPC) was used to determine molecular weights and molecular weight distributions, Mw/Mn, of polymer samples with respect to polystyrene standards (Polysciences Corporation). The system configuration was described by R. F. Storey and T. P. Hickey, *J. Polymer Sci.* 31, 1825 (1993). Throughout this specification, unless otherwise stated, the term "molecular weight" refers to weight average molecular weight.

General Procedure

1. Synthesis of acid-terminated polymers

Glassware was dried at 145–155° C. for 24 h, fitted with rubber septa, and cooled under a flow of dry nitrogen. Polymerizations were run in 250-mL Erlenmeyer flasks with 24/40 ground glass joints sealed with evacuated glass stoppers wrapped with teflon tape. To a flask (250 mL) containing a magnetic stir bar were added D,L-lactide (18.17 g, $1.26 \times 10^{-1}$ mol), glycolide (14.63 g, $1.26 \times 10^{-1}$ mol), ε-caprolactone (7.20 g, $6.30 \times 10^{-2}$ mol), glycolic acid (1.66 g, $2.18 \times 10^{-2}$ mol), succinic anhydride (2.19 g, $2.18 \times 10^{-2}$ mol). The flask was purged with nitrogen and heated in a 135° C. constant temperature bath for 20 h with continuous stirring. At 65 h of reaction, the temperature was lowered to 110° C. The polymerization was allowed to proceed for 146 h and was then quenched in an ice-water bath.

2. Analytical Titration Procedure (2.000 a/mol Sample)

To a 125-mL Erlenmeyer flask was added a (~2,000 g/mol) polymer sample (0.30–0.40 g). The polymer sample was completely dissolved in THF (50 mL), and water (15 mL) was added to the solution. Phenolphthalein (1 g/100 mL MeOH) (5 drops) was added to the polymer solution, and the flask was placed in an ice bath. The sample was titrated with an aqueous solution of NaOH (0.5047 N) to a light pink end point. An average equivalent weight was calculated from the values of at least three titrations.

3. Bulk polymer Titration Procedure (2.000 a/mol Sample)

To a 1,000-mL Erlenmeyer flask was added a (~2,000 g/mol) polymer sample (34.32 g), and the polymer was dissolved in THF (450 mL). The average equivalent weight from analytical titration procedure 2, supra, was used to calculate the exact amount of titrant (85.3 mL, 0.5047 N aqueous NaOH) necessary to completely neutralize the polymer sample. This amount was slowly added to the polymer solution as it was stirred in an ice bath.

EXAMPLES

Example 1

Determination of Adhesive Properties

General Procedure

The adhesion characteristics of the polymers were determined in a tensile test in accordance with the following procedure:

Glass microscope slides were cleaned by first immersing them in a hot sulfuric acid bath for 10 minutes. The slides were rinsed thoroughly with ultrapure water. Then they were placed in a warm ammonium hydroxide:hydrogen peroxide (4:1 by volume) bath for 1 minute. The slides were again rinsed with ultrapure water and dried with filtered nitrogen. The clean glass slides are the dry glass substrates.

Each slide was placed on a holder that exposed 4.84 cm$^2$ of area. An aqueous solution of 3% by weight of polymer in nano-pure water was placed on this exposed area, and the slide was dried under vacuum. All samples were stored in a desiccator before mechanical testing.

Comparison slides for testing adhesion to wet surfaces were made using poly(2-hydroxyethyl methacrylate) (pHEMA). The films of pHEMA were formed using a 4% by weight solution of polymer in methanol, using the procedure described supra. The solution was dried with nitrogen gas followed by 3 hours vacuum.

Mechanical tests were made using a Series 4400 Instron. In order to test the adhesive properties of the polymer film, the glass slide with the test polymer was pressed on a clean dry glass slide with a force of 5 Newtons for 5 minutes. The Instron was then used to measure the stress and strain at which the two glass slides separated by being pulled apart at an angle of about 900 relative to the face of the slide. The separation speed was 0.5 mm per minute.

A separate adhesion test was carried out on the slides made with swollen pHEMA in order to simulate a wet tissue surface. The PHEMA film, cast on glass, was placed in a 100% humidity chamber for 30 minutes before testing. The glass slide with the test polymer was then pressed on the pHEMA slide for 5 minutes at 5 Newtons.

A. Test Results for Homopolymers

The results of these tests with illustrative poly(amino acid) homopolymers are summarized in Table 1.

TABLE 1

| | HOMOPOLYMERS | | | |
|---|---|---|---|---|
| | Glass | | Swollen pHEMA | |
| Polymer* (MW) | max. stress (Pa) | max. strain | max. stress (Pa) | max. strain |
| pGlu (1,000) | 6500 | 0.60 | 0 | 0 |
| pGlu (15,300) | 3400 | 0.65 | 1000 | 0.20 |
| pLys (22,700) | 2800 | 0.30 | 650 | 0.12 |
| pLys (42,000) | 10000 | 0.70 | 2300 | 0.23 |
| pGln (3,500) | 9000 | 0.85 | 0 | 0 |

*All poly (amino acids) were of L configuration

Surprisingly, various homopolymers, such as pGlu (15300), pLys (22700), and pLys (42000) were found to stick to the pHEMA. It was found that all of the homopolymers adhere to the glass surface.

It was determined that the adhesive strength of different materials may be manipulated by changing the homopolymer and/or the molecular weight of the homopolymer. These results can be extrapolated to other amino acids of their class which would be useful in these compositions. In addition, the homopolymers could be substituted with mixed polymers such as copolymers, a terpolymer, block copolymers, or mixtures thereof.

B. Test Results of Polymer-Monomer Complexes

The results of these tests with typical polymer-monomer complexes are illustrated in Table 2.

TABLE 2

POLYMER-MONOMER COMPLEXES

| | Glass | | Swollen pHEMA | |
|---|---|---|---|---|
| Complex (MW) [Wt. Ratio] | max. stress (Pa) | max. strain | max. stress (Pa) | max. strain |
| pGlu(1000):Lys[2:1] | 1100 | 0.12 | 1000 | 0.07 |
| pGlu(1000):Lys[1:2] | 9000 | 0.60 | 0 | 0 |
| pGlu(15300):Lys[2:1] | 8000 | 0.60 | 2300 | 0.40 |
| pGlu(15300):Lys[1:1] | 10000 | 0.80 | 1500 | 0.16 |
| pLys(22700):Glu[1:1] | 0 | 0 | 0 | 0 |
| pLys(22700):Glu[1:2] | 0 | 0 | 0 | 0 |
| pLys(42000):Glu[1:0.8] | — | — | 5500 | 0.50 |
| pLys(42000):Glu[1:2] | 0 | 0 | 1150 | 0.25 |
| pGln:Lys (35000):Lys [1:0.6] | 3500 | 0.30 | 1250 | 0.13 |
| pGln:Lys [1:0.7] | 4800 | 0.65 | 0 | 0 |
| pGln:Lys[1:1] | 0 | 0 | 1200 | 0.20 |
| pGln:Glu[1:1] | 5000 | 0.45 | 0 | 0 |
| pGln:Glu[1:2] | 3000 | 0.30 | 0 | 0 |

It was found that the adhesion of pGlu polymers (1000 and 15300) on glass improved as the amount of Lys monomer was added. On swollen pHEMA, a higher pGlu to Lys monomer ratio favored adhesion. The adhesion of pLys (22700 and 42000) on glass decreased as the amount of Glu monomer increased. Finally, the addition of Glu monomer improved the adhesion of pLys (42000) to swollen PHEMA.

These results demonstrate how a specific adhesive strength to different types of material may be achieved. The type of amino acid homopolymer used, or mole weight of the homopolymer, can be tailored to produce a desired adhesive property to different materials. The homopolymers could be substituted with mixed polymers such as copolymers, a terpolymer, block copolymers, or mixtures thereof.

C. Test Results for Polymer Blend Complexes

The results of these tests with typical polymer blend complexes are illustrated in Table 3.

TABLE 3

POLYMER BLENDS

| Blend of pGln (3500) with amino acid homopolymer (MW) [Wt. Ratio] | Glass | | Swollen pHEMA | |
|---|---|---|---|---|
| | max. stress (Pa) | max. strain | max. stress (Pa) | max. strain |
| pGlu(1000) [1:0.4] | 3000 | 0.40 | 0 | 0 |
| pGlu(1000) [1:0.8] | 5000 | 0.55 | 3300 | 0.25 |
| pGlu(1000) [1:2] | 2800 | 0.55 | 0 | 0 |
| pGlu(15300) [1:0.9] | 7500 | 0.60 | 2300 | 0.30 |
| pGlu(15300) [1:2] | 16000 | 1.50 | 8500 | 1.00 |
| pLys(22700) [1:0.3] | 2000 | 0.20 | 0 | 0 |
| pLys(22700) [1:0.8] | 13000 | 0.95 | 0 | 0 |
| pLys(22790) [1:2] | 6000 | 0.42 | 0 | 0 |
| pLys(24000) [1:0.5] | 1800 | 0.25 | 0 | 0 |
| pLys(42000) [1:0.8] | 9000 | 0.85 | 5500 | 0.90 |
| pLys(42000) [1:0.84] | 11000 | 1.75 | — | — |
| pLys(42000) [1:0.9] | 8000 | 1.40 | — | — |
| pLys(42000) [1:1.2] | 10000 | 0.90 | — | — |
| pLys(42000) [1:1.25] | 13000 | 2.30 | 9000 | 1.10 |
| pLys(42000)[1:2] | 3100 | 0.18 | 3500 | 0.55 |

It was discovered that polymer blends of pGln with pGlu (15300) showed a noticeable improvement over pGln homopolymer (see Table 1) in adhesion and strength and strain on both substrates. The sample pGln:pGlu (15300) [1:2] was one of the most preferred adhesives. The polymer blends of pGln with pLys (42000) were also among the most preferred adhesives. pGln and pLys (42000) by themselves exhibited good adhesion to glass but their blends were even better adhesives.

Blends of amino acid homopolymers were most preferred as adhesives. These tests illustrate a large number of useful combinations of amino acid polymer blends suitable for use in this present invention. The blends may be expanded to three or more polymers and include monomers if needed to customize the adhesive characteristics to the target substrates.

D. Adhesiveness of Certain Polyesters

The results of these tests with typical polyesters are summarized in Table 4.

TABLE 4

POLYESTERS

| Polymer* [Wt. Ratio] | MW | Glass | | Swollen pHEMA | |
|---|---|---|---|---|---|
| | | max. stress (Pa) | max. strain | max. stress (Pa) | max. strain |
| PLG [1:1] | 50,000 | 0 | 0 | 0 | 0 |
| PLG [1:1] | 1,000 | 28,000 | 3.2 | 23,000 | 2.7 |
| PLGC-COOH [2:2:1] | 2,000 | 20,000 | 2.7 | 28,000 | 4.0 |
| PLGC-COONa [2:2:1] | 2,000 | 30,000 | 4.2 | 27,000 | 3.0 |
| PL | 2,000 | 62,000 | 9.0 | 31,000 | 7.0 |

L = lactide; G = glycolide; C = ε-caprolactone

Example 2

Determination of Polymer Water Solubility

1. Dissolve the polymer (50 mg) in tetrahydrofuran (THF) in a 25-mL glass test tube.
2. Evaporate the THF by air drying at room temperature, leaving a thin film of polymer coating the bottom of the test tube.
3. Add water (10 mL) to the test tube; mix the water and the polymer; allow the mixture to stand at room temperature for 24 hours.
4. Pipette the solution into a pre-weighed cup.
5. Evaporate the water under vacuum at 40° C.
6. Weigh the cup containing the polymer and calculate the amount of polymer in solution by subtracting the weight of the empty container.

Example 3

Matrix of PLGC with TGF-β and TCP

| | |
|---|---|
| TCP: | DePuy, 149 μ to 250 μ diameter |
| TGF-$β_1$: | Genetech, 0.73 mg/mL |
| PLGC Polymer: | Poly (lactide: glycolide: ε-caprolactone) (40:40:20) Na+ ionomer (MW 2,000) (See Preparation supra) |
| Coating Buffer: | 20 mM Na acetate, pH 5.0 (Sigma cat # S-5889) |
| Gelatin Buffer: | 2.5% Gelatin (250 mg/10 mL water), 100 Bloom General Foods |
| Rinse Buffer: | PBS pH 7.4, Boehringer Mannheim cat. 100-961 |

-continued

| | |
|---|---|
| Antioxidant: | 0.2% N-propyl gallate in water (20 mg/10 mL; heat in microwave to place in solution) Sigma cat P-3130 |

Procedure
1. Add the desired amount of TGF-$\beta_1$ to the coating buffer (2 mL/g of TCP).
2. Mix the TGF-$\beta_1$ coating buffer solution with dry TCP in a siliconized polypropylene container.
3. Incubate the mixture at room temperature 3 hours with constant, gentle mixing.
4. Let the TCP settle or gently centrifuge; separate the TGF-$\beta_1$ coating buffer by decanting.
5. Add rinse buffer (same volume as coating buffer), mix and separate it by decanting.
6. Repeat rinse step.
7. Add antioxidant solution (same volume as the rinse buffer); mix and separate it by decanting.
8. Add gelatin buffer to the TGF-$\beta_1$-coated TCP (1.25 mL buffer/g TCP).
9. Add TCP/buffer mixture to the viscous PLGC polymer and mix [0.796 g (44%) of polymer/1 g (56%) of TCP].
10. Quickly freeze the matrix with liquid $N_2$
11. Lyophilize the matrix.

The matrix should be stored dry at −70° C. It will readily adsorb water from the atmosphere. The matrix can be sterilized by gamma radiation 2.5 Mrads in a $N_2$ atmosphere in a sealed-foil pack.

Example 4

Dissolution and Release of Matrices of

Polyester Blends

This example demonstrates how the present implant matrices can be modified to adjust degradation and delivery of a biological substance in a desired time frame.
(a) Dissolution Rate
Method TCP (50 mg) was mixed with enough polymer to bind all the TCP. The mixture was dried completely in a vacuum oven. The dry mix was weighed and placed in phosphate buffered saline (PBS) (5 mL). The weight of the matrix that remained bound together was measured daily. Incubation during this process was at room temp. Complete dissolution was defined as the point at which no matrix material remained bound together.

Table 5 summarizes the results of this test with varying blends of PLG (A=12000 MW and B=500 MW).

TABLE 5

DISSOLUTION STUDIES WITH PLG BLENDS

| A/B Ratio[a] | Days to Complete Dissolution |
|---|---|
| 80/20 | 17 |
| 70/30 | 11 |
| 60/40 | 4 |

[a]By % weight

Table 6 summarizes the results of tests made with random PLGC terpolymers in a ratio of 40% L–40% G–20% C with different end groups. Each terpolymer had a molecular weight of 2,000. The ionomer samples were prepared by carboxylating PLGC and then neutralizing the carboxylated material with NaOH.

TABLE 6

DISSOLUTION STUDIES WITH PLGC TERPOLYMERS*

| Polymer End Group | Days to Complete Dissolution |
|---|---|
| OH | 50+ |
| COO 50% Na$^+$ | 30 |
| COO 100% Na$^+$ | 4 |

*PLGC ratio 40:40:20

(b) Release Rate

The release of TGF-$\alpha_1$ from a PLGC/TCP/TGF-$\alpha_1$ matrix, prepared as described in Example 3, was measured.

The TGF-$\alpha_1$ was extracted and assayed by ELISA as follows:

Undiluted horse serum (Sigma Cat # H-1270) and 0.02% by weight sodium azide were added to the sample. The amount of serum used depended upon the TGF-$\alpha_1$ concentration; approximately 0.4 to 1 μg TGF-$\alpha_1$/mL final concentration was targeted. The serum and TCP were incubated for a minimum of 12 hours (overnight) at room temperature with mixing. To remove TCP fines, the material was spun in a microfuge at 500×g for one minute.

The samples were then assayed by an ELISA assay to determine biological activity. The TGF-$\alpha_1$ Capture ELISA protocol was as follows:

Material

| | |
|---|---|
| 1. Solid support: | Dynatech Immulon II, cat# 011-010-3450 |
| 2. Coating buffer: | 0.05M Carbonate buffer pH 9.5 Na$_2$CO$_2$ (5.3 g/L) |
| 3. Capture Mab: | Mab < TGF-$\alpha_1$ > 12H5, Genentech, lot #8268-61 |
| 4. Wash buffer: | PBS, 0.05 % Tween 20 |
| 5. Detection Mab: | Mab < TGF-$\alpha_1$ > 4All-HRP Genetech, lot 16904-30 |
| 6. Standard: | TGF-$\alpha_1$, Genentech, used same lot as unknown samples |
| 7. Substrate: | 3,3',5,5'-tetramethylbenzidine (TMB), Kirkegaard & Perry catalog #50-76-100 |
| 8. Stop solution | 1M H$_2$SO$_4$ |

Procedure

A 96-well microtiter plate was coated with 0.5 μg/mL of Mab 12H5 in coating buffer and held at a temperature of 4° C. overnight at 100 μL/well. The plate was washed with wash buffer for 6 cycles in a Titertek Microplate washer 120, and the last volume of wash buffer was left in the wells. The 96-well plate was incubated for 10 minutes with the wash buffer and then emptied of the wash buffer. The TGF-$\alpha_1$ samples were added to the washed plate and serially diluted in PBS at 100 μL/well. The TGF-$\alpha_1$ samples were then incubated for 1 hour at room temperature. The plates were again washed with wash buffer for 6 cycles. 4A11-HRP conjugate was then added to the plate and diluted to approximately 1:2000 in wash buffer, 100 μL/well. The plate: was then incubated for 1 hour at room temperature. The plates were washed with wash buffer for 6 cycles. Next, 100 μL/well of substrate was added to the plate. The color was allowed to develop for 5 minutes. Then 50 μL/well of stop solution was added. The wavelength was read at 450 nm on a Molecular Devices Vmax.

The O.D. values were curve fit using a log linear regression. Standards of diluted TGF-$\alpha_1$ were used to prepare the calibration curve. The multiple needed to superimpose the regression curve on the calibration curve at an O.D. value in the linear region was used to calculate the unknown concentration.

The results of the tests for release of TGF-$\alpha_1$ from the PLGC/TCP/TGF-$\alpha_1$ matrix are summarized in Table 7:

TABLE 7

RECOVERY OF TGF-α FROM POLYMER MATRIX[a]

| Day | % Recovery of TGF-$\alpha_1$ |
|---|---|
| 1 | 42% |
| 2 | 5.8% |
| 3 | 1% |
| 4 | <1% |
| 5 | <1% |
| 6 | <1% |

[a]44% PLGC (2:2:1) Na ionomer, MW 2,000; 56% TCP; 2 mL TGF-$\alpha_1$/g TCP.

The PLGC/TCP/TGF-$\alpha_1$ matrix studied in this example had a high dissolution rate (as shown in part (a), Table 6, PLGC COO$^-$Na$^+$100%) and also a fast release rate of TGFβ$_1$.

Example 5

Formulation of Ionomer/Submucosa Matrix

Reacients

| | |
|---|---|
| TGF-$\alpha_1$: | Genentech 0.73 mg/mL |
| PLGC Polymer: | Poly (lactide: glycolide: ε-caprolactone) (40:40:20) Na ionomer; MW 2,000 |
| Coating Buffer: | 20 mL Na acetate, pH 5.0, (Sigma); 1% gelatin final concentration during coating (100 Bloom General Foods) |
| Antioxidant: | 0.2% N-propyl gallate in water |
| Small Intestinal Submucosa (SIS): | (Prepared in accordance with U.S. Pat. Nos. 4,902,508 and 4,956,178, supra, comminuted and lyophilized) |

Procedure

1. Mix the desired amount of TGF-$\alpha_1$ with coating buffer and submucosa (1 mL buffer/100 mg submucosa) to form a putty.
2. Incubate the mixture for 1 hour at room temperature.
3. Add antioxidant solution to the polymer and stir briefly at room temperature until a viscous solution is produced (4 mL of 0.02% by weight of antioxidant/g of polymer).
4. Mix the submucosa/TGFβ$_1$ mixture with the viscous polymer solution.
5. Place the matrix in a container that: (a) can be frozen in liquid N$_2$ and (b) is shaped so the material can be coated evenly by the polymer, i.e., a glass petri dish.
6. Quickly freeze the matrix with liquid N$_2$.
7. Lyophilize the matrix.
8. Sterilize the polymer/matrix formulation as described in Example 3.

The polymer matrix prepared by this procedure had a final composition of 67% polyester ionomer, 33% submucosa and contained 5 μg/mL TGF-$\alpha_1$.

Example 6

Polyester Solubility

The solubility of various polyesters was measured using the procedure of Example 2. The results of these studies are summarized in Table 8.

TABLE 8

SOLUBILITY OF POLYESTERS

| Polymer | Ratio | (MW) | Solubility (g/L) |
|---|---|---|---|
| PL | — | 200 | 0.01 |
| PLG | 1:1 | 1000 | 1.4 |
| PLGC - OH | 2:2:1 | 2000 | 0.2 |
| PLGC - COOH | 2:2:1 | 2000 | 0.3 |
| PLGC - COONa | 2:2:1 | 2000 | 250 |

Example 7

Repair of Rabbit Radius with Matrix Implant

A putty-like delivery matrix including polymer, filler and a biologically active component (TGF-$\alpha_1$) (see Example 3) was evaluated in vivo in the rabbit radius model.

EXPERIMENTAL DESIGN

Route of Administration

A test article, or the autogenous control, is implanted in the midshaft radial defect.

Overview

A 1.5-cm segment of the right radius is removed, producing a unilateral radial defect. The radial defect is implanted with a test material or a control article, or receives no implant, according to group assignment. The incision is closed, and the rabbits are allowed to survive for 8 weeks. At 8 weeks both radii are harvested.

Experimental Procedure

Xylazine/ketamine cocktail is used as the anesthetic agent. The cocktail is made by mixing xylazine (1.42 mL; 100 mg/mL) in ketamine (10 mL; 100 mg/mL). The rabbits are dosed initially at approximately 0.65 mL/kg I.M. (maximum of 3 mL per rabbit). An ear vein is catheterized, and additional anesthesia is given through this catheter at approximately 0.125 of the initial dose, as needed. The right radius is clipped free of hair, then shaved or depilitated and aseptically prepared for surgery.

Surgery

An incision is made mid-shaft over the anterior-medial surface of the right forearm. Soft tissue is reflected to expose the radius. The interosseous ligament between the radius and the ulna is separated, and the periosteum is excised from the radius for approximately 1.7 cm along the mid-shaft. A sterile spatula is placed between the radius and the ulna, and a 1.5 cm segment of the radius is removed, using a saw blade attached to a sagittal saw. The site is liberally irrigated with physiological saline during the ostectomy to prevent overheating of the bone margins.

Experimental Sequence

Each radial defect is filled with one of the test materials or the autogenous graft or is left empty. After the material is molded into position, the soft tissue is reapposed with absorbable suture and the skin is closed with non-absorbable suture.

The amount of material actually implanted is determined by weighing the formulation after preparation, before implanting (using a sterile foil weighing boat or a similar device), and then weighing the material not implanted.

The surgical site is radiographed to document the anatomic placement of the material, and the rabbits are returned to their cages. Buprenorphine hydrochloride (0.15 mg SQ) is administered daily for the first 3 days of recovery for pain.

The rabbits are maintained post surgery for 8 weeks and then terminated with Beuthanasia-D® Special Solution administered intravenously. The right and left radii are removed, and soft tissue is dissected free from these bones. The operated radius is examined histologically for the presence of bone within the defect site (indicating a union) and the presence of cartilage, soft tissue or cracks within the defect site (indicating a possible unstable union or nonunion). The results are scored histologically according to the scale: 0=failed, 1=poor, 2=moderate, 3=good, and 4=excellent.

The results of a study made using this procedure are summarized in Table 9.

TABLE 9

RABBIT RADIUS STUDY WITH PLGC IONOMER/TGF-$\alpha_1$ MATRIX

| Treatment | Average Score | Std. Dev. | n[b] |
|---|---|---|---|
| Autograft (+ control) | 3.4 | 0.5 | 20 |
| Empty (− control) | 0.8 | 1.4 | 20 |
| Polymer[a]/TCP | 0 | 0 | 10 |
| Polymer[a]/TCP/TGF-$\alpha_1$ (γ-sterilized) | 3.8 | 0.3 | 10 |

[a]PLGC COONa (2:2:1; MW 2,000)
[b]n = number of animals

This test demonstrated that the matrices of this invention can be used to repair long bones like the radius, which contain marrow, have a rich blood supply, and experience mechanical loading.

Example 8

Handinging/Moldability of Polymer Matrices

The handling characteristics of the polymer implant matrices during surgical procedures is very important. The putty-like matrix should be moldable enough to be formed to fit into a defect site, and adhesive enough to remain in the defect site. The putty matrix should not, however, be so adhesive that it will adhere easily to surfaces such as surgeon's latex gloves or surgical instruments. This example shows how a typical polymer adhesive matrix was designed to meet these requirements.

TCP (50 mg) was soaked with water (1 μL/mg); than polymer (See Table 10 for amount) was mixed with the TCP solution. The mixture was dried with vacuum or lyophilized. The putty adhesive matrices were measured by the following criteria: (1) moldability—hard or soft; (2) adherence to latex gloves; and (3) adherence to instruments.
Polymers Tested
    PLG 50–50=50% lactide, 50% glycolide random copolymer
    PLGC 40–50–10=40% lactide, 50% glycolide, 10% caprolactone random terpolymer
    PLGC 40–40–20=40% lactide, 40% glycolide, 20% caprolactone random terpolymer
    PLGC 40–40–20 COOH=PLGC 40–40–20 carboxylated with succinic anhydride
    PLGC 40–40–20 COONa=PLGC 40–40–20 COOH neutralized with NaOH to produce COO⁻ Na⁺ end groups
The results of the handling tests using these polymers are summarized in Table 10.

TABLE 10

HANDLING/MOLDABILITY STUDY RESULTS

| Polymer | Mol. Wt. | Amt. of polymer (mg) | Moldability | Adherence to gloves, instruments |
|---|---|---|---|---|
| PLG 50-50 | 12,000 | 20 | No/hard | No |
| PLG 50-50 BLEND | 10% = 12,000 90% = 400 | 30 | Yes | Yes |
| PLG 50-50 | 1,400 | 50 | No/hard | No |
| PLG 50-50 | 700 | 60 | Yes | Yes |
| PLGC 40-50-10 | 2,000 | 40 | No/hard | No |
| PLGC 40-40-20 | 2,000 | 40 | Yes | Yes |
| PLGC 40-40-20 COOH | 2,000 | 40 | No/hard | Yes |
| PLGC 40-40-20 COONa | 2,000 | 35 | Yes | No |

This example demonstrates how changing the molecular weight, composition, and end groups influences the moldability and adherence qualities of the matrix. By lowering the molecular weight of PLG, the composition became more moldable, but also stickier to latex gloves. When the percentage of caprolactone was increased, the moldability increased, but so did adherence to gloves. Adding the carboxyl group to the terpolymer hardened the polymer, but neutralization of the carboxylated terpolymer produced a moldable putty that did not adhere to latex gloves. The PLGC 40–40–20 Na example included TCP as a filler of solid support. If another filler is used, the composition can be tailored in a similar manner to produce a putty-like implant matrix having the desired characteristics.

Example 9

Effect of Glass Transition Temperature on Polymer Handling

Differential scanning calorimetry (DSC) is a commonly used technique of thermal analysis. During a DSC measurement, the reference pan and sample pan are heated such that their temperature increases at a constant predefined rate. The difference of heat flow to reference pan and sample pan is measured. When the heat flow to sample pan is greater than that to reference pan, the measured heat flow difference is endothermic. When the heat flow to sample pan is less, the measured heat flow difference is exothermic.

DSC analysis of polymers gives information on glass transitions ($T_g$). A $T_g$ is found in all amorphous polymers and in amorphous regions of partially crystalline polymers. The $T_g$ of the latter is independent of the degree of crystallization, but the magnitude of the transition decreases with increasing crystallinity so the transition becomes difficult to detect in highly crystalline polymers. A polymer at temperatures above its $T_g$ is limp and flexible, but a polymer below $T_g$ is brittle and stiff. (See M. C. Meikel, W. Y. Mak, S. Papaionannou, E. H. Davies, N. Mordan, J. J. Reynolds, *Biomaterials*, 14(3), 177 (1993); and J. L. Ford, P. Timmins, "*Pharmaceutical Thermal Analysis*", Chapter 2, John Wiley & Sons, New York (1989).)

This example demonstrates that $T_g$ can be a valuable tool to determine if a polymer will remain moldable. The maximum and minimum $T_g$ temperatures may be slightly different for different applications and or solid substrates. This example used TCP as the solid substrate.

The results of these tests are summarized in Table 11.

TABLE 11

GLASS TRANSITION AND HANDLING CHARACTERISTICS

| Polymer | MW | Ratio | $T_g$ (° C.) | Handling[a] |
|---|---|---|---|---|
| PLG Blend | 12,000 | 1:1 | 42.9 | hard |
| 50% PLG | 12,000 | 1:1 | 20.4 | hard |
| 50% PLG | 4,000 | 1:1 | | |
| PLG | 8,500 | 1:1 | −3.1 | crumbles |
| PLG | 3,500 | 1:1 | −13.3 | will mold |
| PLGC | 2,000 | 5:4:1 | −16.0 | hard but will mold |
| PLGC Blend | 2,000 | 2:2:1 | −28 | most moldable |
| 90% PLG | 500 | 1:1 | −26.9 | moldable |
| 10% PLG | 8,500 | 1:1 | | |

[a]at room temperature

Modifications and variations of the polymers, implant matrices and methods of this invention will be apparent to those skilled in the art from this description. Such modifications and variations are intended to be within the scope of the appended claims.

What is claimed is:

1. A pressure sensitive adhesive for tissue repair comprising an α-hydroxycarboxylic acid terpolymer that has an average molecular weight of 1,000 to 3,000, exhibits an adhesive strength of about 600 to about 150,000 Pa and has a water solubility of 0.01 to about 500 mg/ml at about 25° C., wherein the terpolymer is poly(lactide/glycolide/caprolactone) and comprises about 35–45% lactide, about 35–45% glycolide, and about 10 to about 30% caprolactone.

2. The pressure sensitive adhesive of claim 1 wherein the terpolymer has a glass transition temperature of less than 0° C.

3. The pressure sensitive adhesive of claim 1 further comprising a filler.

4. The pressure e sensitive adhesive of claim 1 further comprising a bioactive agent.

5. The pressure sensitive adhesive of claim 3 wherein the filler is selected from the group consisting of bone chips, tricalcium phosphate, hydroxylapatite, small intestine submucosa, bioglass granules, synthetic polymers, calcium carbonate, calcium sulfa and collagen.

6. The pressure sensitive adhesive of claim 4 wherein the bioactive agent is a growth factor.

7. The pressure sensitive adhesive of claim 6 wherein the growth factor is selected from the group consisting of a fibroblast growth factor, a transforming growth factor, a bone morphogenetic protein, an epidermal growth factor, a platelet-derived growth factor and an insulin-like growth factor.

* * * * *